United States Patent [19]

Reuter et al.

[11] 4,411,818

[45] Oct. 25, 1983

[54] REACTIVATION OF VANADIUM-CONTAINING OXIDATION CATALYSTS

[75] Inventors: Peter Reuter, Ludwigshafen; Kurt Blechschmitt, Schifferstadt; Friedrich Wirth, Ludwigshafen, all of Fed. Rep. of Germany

[73] Assignee: BASF Aktiengesellschaft, Fed. Rep. of Germany

[21] Appl. No.: 348,198

[22] Filed: Feb. 12, 1982

[30] Foreign Application Priority Data

Mar. 4, 1981 [DE] Fed. Rep. of Germany ....... 3108101

[51] Int. Cl.$^3$ .................. B01J 23/92; B01J 21/20; B01J 27/28; C07D 307/89
[52] U.S. Cl. ..................... 502/35; 260/369; 549/248; 549/257; 549/258; 549/259; 502/37
[58] Field of Search ............. 252/41 R, 416, 415; 549/248

[56] References Cited

U.S. PATENT DOCUMENTS

| | | | |
|---|---|---|---|
| 3,474,041 | 10/1969 | Kerr | 252/411 R |
| 4,007,136 | 2/1977 | Blechschmitt et al. | 252/476 |
| 4,035,399 | 7/1977 | Yokoyama | 549/248 |
| 4,036,783 | 7/1977 | Blechschmitt et al. | 252/461 |
| 4,123,442 | 10/1978 | Bakshi | 252/416 |

FOREIGN PATENT DOCUMENTS

| | | |
|---|---|---|
| 2436009 | 2/1976 | Fed. Rep. of Germany . |
| 2510994 | 9/1976 | Fed. Rep. of Germany . |
| 368229 | 1/1973 | U.S.S.R. ............... 549/248 |

Primary Examiner—P. E. Konopka
Attorney, Agent, or Firm—Keil & Witherspoon

[57] ABSTRACT

A process for reactivating a vanadium-containing oxidation catalyst, wherein the catalyst is treated first at from 100° to 600° C., with a volatile phosphorus compound in the presence of an oxygen-containing gas, and then at from 50° to 600° C. with sulfur trioxide or a mixture of a volatile sulfur compound and an oxygen-containing gas.

4 Claims, No Drawings

REACTIVATION OF VANADIUM-CONTAINING OXIDATION CATALYSTS

The present invention relates to a process for reactivating vanadium-containing oxidation catalysts. These catalysts are conventionally used for the preparation of carboxylic acids, carboxylic acid anhydrides or quinones by oxidation of saturated or unsaturated aliphatic or aromatic hydrocarbons. The oxidation is carried out industrially in the vapor phase, using air, in a fixed bed or fluidized bed reactor.

Vanadium-containing catalysts which have become important for large-scale industrial processes are, for example, those used for the preparation of phthalic anhydride (PA) from o-xylene or naphthalene, of maleic anhydride (MA) from benzene or saturated or unsaturated aliphatic hydrocarbons of 4 to 6 carbon atoms, or of anthraquinone from diphenylmethane compounds. Catalysts of this type which contain vanadium, for example in the form of vanadium pentoxide, together with titanium dioxide, and whose active material also contains other active constituents, for example the oxides of cesium, rubidium, phosphorus or antimony, are described, for example, in German Laid-Open Applications DOS Nos. 2,436,009 or 2,510,994.

These vanadium-containing catalysts have the disadvantage that they undergo a continuous loss of activity during operation. To maintain an adequate conversion, it is therefore necessary to employ increasingly severe reaction conditions. This can be effected, for example, by increasing the reaction temperature, lowering the throughput of air, or decreasing the loading, of the air or of the carrier gas, with the hydrocarbon to be oxidized.

The loss in yield associated therewith, or the decrease in capacity, finally becomes so great that the catalyst can no longer be used economically and must be replaced. This is an expensive procedure, since the plant has to be shut down for weeks, giving rise to loss of production. Additionally, the catalysts are expensive.

Attempts have therefore been made to counteract the deactivation of the catalysts by continually adding activating substances to the catalyst. Sulfur dioxide is added, for example, in the oxidation of o-xylene to give PA. Without continual addition of these activators, the catalyst loses activity even more rapidly, and the operating conditions have to be rapidly made more severe to maintain the desired results. Some or all of the activator, eg. $SO_2$, leaves the plant unchanged and therefore pollutes the environment; its removal from the waste gases leaving the plant is very expensive.

It is an object of the present invention to provide a process for reactivating completely or partially deactivated vanadium-containing catalysts, which makes it unnecessary continually to add activators while the catalyst is in use, and makes it possible to maintain high yields and throughputs in the catalytic oxidation.

We have found that this object is achieved by the process according to the invention, in which the reactivation of a vanadium-containing oxidation catalyst is effected as follows: the catalyst is treated first at from 100° to 600° C., with a volatile phosphorus compound in the presence of an oxygen-containing gas, and then at from 50° to 600° C. with sulfur trioxide or a mixture of a volatile sulfur compound and an oxygen-containing gas.

Although German Published Application DAS No. 1,468,816 discloses that oxidation catalysts containing vanadium and phosphorus can be reactivated by the addition of phosphites, the novel process is not suggested by this procedure since the advantageous results of the process of the invention are not obtained when the catalyst is treated with the phosphorus compound or the sulfur compound alone, or when the substances are employed for treatment in the reverse sequence.

Suitable volatile phosphorus compounds are those which are volatile at the temperatures of the reactivation according to the invention, examples being phosphines, eg. trimethylphosphine, phosphine oxides, eg. trimethylphosphine oxide, hydrogen phosphide, phosphorus oxides, eg. phosphorus pentoxide, phosphates or phosphites, eg. $OP(O[CH_2]_3CH_3)_3$, phosphorus halides, eg. phosphorus trichloride, phosphorus oxyhalides, eg. phosphorus oxychloride, or phosphorus sulfohalides.

In addition to sulfur trioxide, preferred volatile sulfur compounds are those which are converted under the reactivation conditions, with air or another oxygen-containing gas, or with a catalyst, completely or in part into sulfur trioxide, for example sulfur dioxide, hydrogen sulfide, mercaptans, eg. ethylmercaptan, carbon disulfide, elementary sulfur, sulfur halides, eg. sulfur dichloride, and sulfur oxyhalides, eg. thionyl chloride.

Particularly good results are obtained when triphenylphosphine is used as the phosphorus compound and $SO_3$ or $SO_2$ as the sulfur compound.

The novel process is particularly suitable for reactivating vanadium-containing catalysts used for the oxidation of o-xylene or naphthalene to PA. Such catalysts which are described, for example, in German Laid-Open Application DOS No. 2,510,994, are supported catalysts consisting of an inert carrier and a catalytically active material which is applied onto the carrier, contains, for example, from 1 to 30% by weight of vanadium pentoxide and from 70 to 99% by weight of titanium dioxide, and can also contain small amounts, for example up to 5% by weight, of other activators, eg. rubidium oxide, cesium oxide, phosphorus pentoxide and antimony trioxide.

For the production of PA, a catalyst of this type is conventionally placed in a tube oven whose tubes have a diameter of from 18 to 40 mm and a length of from 1.0 to 4.0 m, and are surrounded by a salt melt, kept at from 340° to 450° C., for regulating the temperature. The gaseous mixture of air and the hydrocarbon to be oxidized is passed through the tube oven.

The novel reactivation process is carried out, for example, as follows: the air or another oxygen-containing gas is preheated to from 20° to 500° C., advantageously from 100° to 300° C., the phosphorus compound is then added to the gas, and the mixture is passed over the catalyst in a tube reactor. The catalyst is heated to 100°–600° C., advantageously to 200°–500° C., by the heat transfer medium circulating through the reactor tubes. The amount of phosphorus compound used provides from 1.0 to 10,000, advantageously from 10 to 1,000, mg of phosphorus per 100 g of catalytic material in the catalyst. The amount of air laden with the phosphorus compound, or of the carrier gas, is from 0.01 to 8.0, advantageously from 0.1 to 5.0, m³ (S.T.P.) per hour per 100 g of catalytic material. The mixture of the phosphorus compound and the air or carrier gas contains from 0.01 to 10,000, advantageously from 0.1 to 1,000, mg of phosphorus per m³ of gas.

In a particularly advantageous embodiment of the invention, the phosphorus compound required for activating the catalyst is added during operation, ie. during the oxidation of, for example, o-xylene with air, since it is thus not necessary to interrupt the production of PA, and particularly rapid and good activation is obtained. For this purpose, the liquid or gaseous phosphorus compound is added to the carrier gas before the latter is passed into the reactor. The phosphorus compound can also be dissolved in liquid o-xylene and added together therewith to the air.

The amount of air or carrier gas per 100 g of catalytic material is from 0.5 to 8.0, advantageously from 1.0 to 6, m$^3$ (S.T.P.) per hour, the concentration of o-xylene in the carrier gas is from 20 to 150 g/m$^3$ (S.T.P.), and the concentration of phosphorus, in the form of phosphorus compounds, in the carrier gas is from 0.01 to 10,000, advantageously from 0.1 to 1,000, mg/m$^3$ (S.T.P.). The amount of phosphorus per 100 g of catalytic material is from 1.0 to 10,000, advantageously from 10 to 1,000, mg.

The salt melt, which regulates the temperature of the reactor, is at from 300° to 500° C., advantageously at from 340° to 450° C. The oxygen-containing carrier gas is heated to 60°–500° C., advantageously to 100°–300° C., before the addition of o-xylene and the phosphorus compound.

The duration of treatment with the phosphorus compound, or the amount of the latter acting on the catalyst, varies from case to case, depending on the residual activity of the catalyst.

After treatment with the phosphorus compound, the catalyst still shows no activation, and frequently undergoes still further loss of activity as a result of the treatment. This loss is evident from the need to increase the temperature of the salt during the reaction of o-xylene with air or with the oxygen-containing carrier gas.

A noticeable and permanent activation is obtained only after or during the subsequent treatment of the catalyst with the sulfur compound, a procedure which can be carried out in various ways. If SO$_3$ is used, it can be employed alone, or mixed with air or the carrier gas, with or without o-xylene. If SO$_2$ or another volatile sulfur compound is used, it is employed together with the oxygen-containing carrier gas, with or without the admixture of o-xylene.

When the catalyst is treated with SO$_3$, with SO$_3$ mixed with air or the carrier gas, or with SO$_2$ or another sulfur compound mixed with the oxygen-containing carrier gas, these substances or oxygen mixtures are passed over the catalyst, or the catalyst is placed under these substances or mixtures of substances. The catalyst must be at from 50° to 600° C., advantageously at from 300° to 500° C.

If SO$_3$ is used in a mixture with a carrier gas, the latter need not necessarily contain oxygen. Examples of oxygen-free carrier gases are nitrogen or carbon dioxide.

Mixtures of SO$_3$, SO$_2$ or another sulfur compound with air or the carrier gas are passed over the catalyst in an amount of from 0.1 to 8.0, advantageously from 1.0 to 5.0, m$^3$ (S.T.P.) per hour per 100 g of catalytic material.

If mixtures of the sulfur compounds with the oxygen-containing carrier gas are employed, the latter can be laden with o-xylene. In this case, the salt melt for regulating the temperature is at from 300° to 500° C., advantageously at from 340° to 450° C.

The amount of gas mixture passed over the catalyst is from 0.5 to 8.0, advantageously from 1.0 to 6, m$^3$ (S.T.P.) per hour. The concentration of o-xylene can be up to 150 g per m$^3$ (S.T.P.) of gas mixture.

The concentration of SO$_3$, SO$_2$ or a suitable sulfur compound in the air or in the carrier gas, which can also be laden with o-xylene, can be varied within wide limits. The procedure is advantageously carried out using an excess of air or carrier gas, particularly when the latter is laden with o-xylene.

The amount, of SO$_3$, SO$_2$ or another sulfur compound, necessary for activating the catalyst varies from case to case, depending, inter alia, on the degree of deactivation of the catalyst before activation. This amount can be found experimentally by determining the activity of the catalyst during or after the activation in the oxidation of o-xylene to give PA. Repeated treatment with SO$_3$, SO$_2$ or a sulfur compound may be necessary, until an increase in the activity of the catalyst is no longer observed.

The sulfur compounds are added in liquid or gaseous form to the air or the carrier gas. Sulfur compounds which are soluble in, or miscible with, o-xylene are advantageously added, together with the latter, to the air or the carrier gas.

EXAMPLE (a) Preparation of phthalic anhydride (PA) by the oxidation of o-xylene with air over a vanadium-containing supported catalyst.

4.0 m$^3$ (S.T.P.)/hour of air laden with 60 g/m$^3$ (S.T.P.) of 97% strength by weight o-xylene are passed downwards through a reactor which has a length of 3.25 m and an internal diameter of 25 mm, and the temperature of which is regulated by a circulating salt melt at 374° C. The reaction gases are cooled and the PA formed separates out.

The tubular reactor contains two different catalysts, the first in the direction of flow occupying 1.20 m and the second occupying 1.60 m (a total of 2.80 m). The first catalyst consists of an inert carrier coated with a catalytically active material containing 7% by weight of vanadium pentoxide, 0.13% by weight of rubidium in the form of rubidium oxide, and 92.87% by weight of titanium dioxide in the form of anatase. The second catalyst consists of an inert carrier coated with a catalytically active material containing 7% by weight of vanadium pentoxide, 0.5% by weight of phosphorus in the form of phosphorus pentoxide, and 92.5% by weight of titanium dioxide in the form of anatase. The total amount of catalytic material in the catalysts contained in the reactor is 116 g.

After 300 days' operation, the yield of PA is 112% by weight (based on 100% strength o-xylene). The PA produced contains 0.01% by weight of phthalide.

After 460 days' operation, the temperature of the salt melt has to be increased to 394° C. to keep the phthalide content of the PA produced below 0.03%, and the yield of PA has decreased to 104% by weight.

(b) Reactivation of the catalyst:

After 461 days' operation in the oxidation of o-xylene to give PA under the conditions given in (a), 1 g of triphenylphosphine is added to the o-xylene before it is passed over the catalyst, without interrupting the oxidation. The concentration of triphenylphosphine in the o-xylene is 0.5% by weight.

The supply of o-xylene to the reactor is then interrupted, and an atmosphere consisting of a mixture of air and SO₂ in the volume ratio 5:1 is introduced over the catalyst, with the salt melt at 394° C., for 32 hours.

After the reactor is brought into operation again by passing in 4 m³ (S.T.P.)/hour of air which is laden with 60 g of o-xylene/m³ (S.T.P.), the temperature of the salt melt can be decreased from 394° to 388° C., without the phthalide content of the PA produced increasing to above 0.03%.

After 2 days' operation, the above 32-hour treatment of the catalyst with the mixture of air and SO₂ is repeated. After the reactor is brought into operation under the above conditions, the temperature of the salt melt can be decreased to 378° C. The PA produced contains less than 0.03% by weight of phthalide, and the yield of PA has increased to 110% by weight.

9 months after the catalyst has been activated as described in this Example, an increase in the temperature of the salt melt is still not required. The PA produced contains less than 0.03% by weight of phthalide, and the yield of PA remains unchanged at 110% by weight.

We claim:

1. A process for reactivating a supported catalyst used for the preparation of phthalic anhydride by the oxidation of o-xylene or naphthalene, said catalyst including an inert carrier and active material applied to the carrier, said active material consisting essentially of from 1 to 30% by weight of vanadium pentoxide, from 70 to 99% by weight of titanium dioxide and up to 5% by weight of oxides of rubidium, cesium, phosphorus or antimony, which process comprises: treating the catalyst in a first stage at from 100° to 600° C. with a phosphorus compound that is volatile at the reactivation temperature in the presence of an oxygen-containing gas, said phosphorus compound being a phosphine, phosphine oxide, hydrogen phosphide, phosphorus oxide, phosphate, phosphite, phosphorus halide, phosphorus oxyhalide or phosphorus sulfohalide; and thereafter treating the catalyst at from 50° to 600° C. with sulfur trioxide or a mixture of an oxygen-containing gas and at least one of sulfur dioxide, hydrogen sulfide, a mercaptan, carbon disulfide, sulfur, a sulfur halide or a sulfur oxyhalide, said sulfur compound being volatile at the reactivating temperature.

2. The process of claim 1, wherein triphenylphosphine is used as the volatile phosphorus compound.

3. The process of claim 1, wherein sulfur dioxide is used as the volatile sulfur compound.

4. The process of claim 1, wherein, in the preparation of phthalic anhydride by the oxidation of o-xylene over said vanadium-containing catalyst at from 300° to 500° C., the volatile phosphorus compound is passed, together with the o-xylene and the oxygen-containing gas, over the catalyst.

* * * * *